US012709762B2

(12) United States Patent
O'Farrell et al.

(10) Patent No.: US 12,709,762 B2
(45) Date of Patent: Aug. 18, 2026

(54) APPROACH FOR BIOGAS GENERATION

(71) Applicant: SixRing Inc., Calgary (CA)

(72) Inventors: Corynne O'Farrell, Calgary (CA); Julie Greer, Calgary (CA); Alexandra Ostaszewski, Calgary (CA); Markus Weissenberger, Calgary (CA); Alejandra Enriquez, Calgary (CA)

(73) Assignee: SixRing Inc., Calgary (CA)

( * ) Notice: Subject to any disclaimer, the term of this patent is extended or adjusted under 35 U.S.C. 154(b) by 323 days.

(21) Appl. No.: 18/447,863

(22) Filed: Aug. 10, 2023

(65) Prior Publication Data

US 2024/0052375 A1 Feb. 15, 2024

(30) Foreign Application Priority Data

Aug. 12, 2022 (CA) ................................ CA 3170346

(51) Int. Cl.
*C12P 5/02* (2006.01)
*C12M 1/107* (2006.01)

(52) U.S. Cl.
CPC ............ *C12P 5/023* (2013.01); *C12M 21/04* (2013.01)

(58) Field of Classification Search
None
See application file for complete search history.

(56) References Cited

U.S. PATENT DOCUMENTS

2021/0269971 A1* 9/2021 Purdy .................... D21C 3/006

FOREIGN PATENT DOCUMENTS

| | | | | |
|---|---|---|---|---|
| CA | 3110553 | A1 | 8/2021 | |
| CA | 3110555 | A1 | 8/2021 | |
| CA | 3110558 | C | 2/2023 | |
| WO | WO-2024031174 | A1 * | 2/2024 | .............. C12P 5/023 |

OTHER PUBLICATIONS

Ma et al. Energy. 189 (Year: 2019).*

* cited by examiner

*Primary Examiner* — Blaine Lankford
(74) *Attorney, Agent, or Firm* — Berg Hill Greenleaf Ruscitti LLP

(57) ABSTRACT

A process to increase the amount of methane produced from a bio-digester comprises providing a digester to receive a feed and to capture a biogas composition resulting from bio-digestion. Organic material is added to the digester along with at least one inoculum capable of converting a portion of the organic material into methane under anaerobic conditions. A biomass is provided that is substantially free of lignin in an amount that ranges between 0.1 to 5% w/w of the total feed, the biomass further having another organic material. The biomass is added to the digester. Sufficient time is allowed for the digester to degrade the biomass and the organic material to yield a biogas composition that includes methane. Optionally, the biomass that is substantially free of lignin is added in an amount that ranges between 0.1 to 5% w/w of the total feed of the biomass having the other organic material.

10 Claims, 7 Drawing Sheets

APPROACH FOR BIOGAS GENERATION

CROSS REFERENCE TO RELATED APPLICATION

This application claims the benefit of and priority to Canadian Patent Application No. 3,170,346, filed Aug. 12, 2022. The entire specification and figures of the above-referenced application are hereby incorporated in its entirety by reference.

FIELD OF THE INVENTION

The present invention is directed to the use of a cellulose in the generation of biogas, more specifically, in the use of a low-lignin content cellulose as an additive to organic matter in a biodigester.

BACKGROUND OF THE INVENTION

Biogases are the product of microbial degradation of various organic materials (both plant-based and animal-based products) in the absence of oxygen, i.e., in an anaerobic environment. This microbial degradation in an oxygen-free environment is called anaerobic digestion. Biogas can refer to gas produced naturally and industrially and generally contains between 45-75 percent methane ($CH_4$ or renewable natural gas RNG), 25-45 percent carbon dioxide ($CO_2$), and trace amounts of various other gases.

Natural sources of biogas include environments such as swamps, which generate methane by action of methanogens. A more common source of biogas is related to industrial activities related to waste disposal, principally related to landfills. A second, less widespread, source of biogas from human activities comes from anaerobic digesters and is used to generate methane and recycle organic waste to be used in fertilizing the field. Biogas is generated when organic waste is exposed to microbes, i.e., bacteria, archaea, and fungi, under anaerobic conditions (no oxygen present) to break down the organic compounds. This biodegradation yields gas (biogas), liquids and solids. The latter two, called digestate, can be used as soil amendments in fields for agriculture. The composition and nutrient content of the digestate is greatly impacted by the feedstock that undergoes bio-digestion.

One of the end uses of industrially generated biogas is to burn it to provide a source of heat and to generate electricity for buildings, boilers and perhaps even the biodigester. Biogas from landfills and digesters can also be refined to separate the methane (natural gas) from the other non-desirable constituents of biogas such as, but not limited to, carbon dioxide, water vapor, hydrogen sulfide, and others. This refining step yields renewable natural gas (RNG) which can be used as is, can be injected into an existing natural gas grid, or even used for vehicles powered by natural gas.

A significant benefit of biogas recovered from biodigesters or landfills is the reduction of usage of fossil fuels. Use of biogas generated from biodigesters or landfills can provide a clean source of power, which also happens to reduce the amount of methane released into the atmosphere. Since natural gas (methane) is a greenhouse gas which is, pound for pound, over 20 times more dangerous to the atmosphere than carbon dioxide over a 20-year period, it is desirable to reduce the release of this gas into the atmosphere. By controlling the release of this gas from its main industrial sources, it is possible to harness the energy it provides, while providing a green and sustainable alternative to power generation. Anaerobic digestion provides additional benefits to communities and the environment such as reducing odours, pathogens, and the risk of water pollution associated with manure coming from livestock and improving soil health.

The United States currently has over 2,000 biogas systems spread out across the country, but it has the potential to add at least another 10,000 additional plants; thus, having a significant positive impact of the environment. In fact, proper harnessing of the potential of biogas in the United States alone would be the equivalent of removing the emissions of millions of cars yearly.

In addition to environmental benefits, the increased implementation of anaerobic digesters using various agricultural and food waste would inevitably reduce the costs associated with waste management if such were simply directed to landfills. Additional advantages of greater implementation of biodigesters in the United States include the building of thousands of biogas systems, which would support hundreds of thousands of construction jobs and the resulting biodigester plants would employ several tens of thousands of people to operate them.

Wastewater treatment plants can have on-site anaerobic digesters to treat sewage sludge recovered during treatment. The solids are separated while the water is released and, more often than not, the methane generated is simply burnt into the atmosphere (i.e., it is flared) without benefiting of the energy this combustion generates. Only roughly two thirds of wastewater treatment plants in the United States that have anaerobic digesters actually use the biogas they generate.

Biogas Feedstocks

Food waste in landfills is responsible for over 20% of the volume of waste present in U.S. landfills. This food waste is an important source of natural gas as it breaks down. While landfills may capture the resultant biogas, putting organic wastes in landfills does not enable operators to recover the nutrients generated from the source organic material such as fats, oils, and grease collected from the food service industry (added to an anaerobic digester to increase biogas production).

Livestock waste is another important source of methane. An average dairy cow weighing 1000 pounds produces approximately 80 pounds of manure per day, which is a non-negligible source of methane. It was assessed, in 2015, that livestock waste contributed to 10% of all methane emissions in the United States but that only 3% of all manure was actually being recycled in biodigester plants. This is a significant lost opportunity as well as environmentally careless.

Organic waste in landfills produces biogas, which is released into the atmosphere. Methane generated from landfills are ranked as the third largest source of such gas (by volume) related to human activities in the United States. Microorganisms present in landfills are similar to those found in bio-digesters, in that they are capable of breaking down organic materials and generating biogas. As methane is a potent greenhouse gas, it is desirable to capture these emissions to utilize them as a potential source of energy.

Crop residues are a source of organic material which can be processed in an anaerobic digester. These residues are meant to include, but not be limited to, stalks, straw, and plant trimmings. There are sufficient crop residues to leave a portion on the field in order to reduce the amount of soil erosion and harvest the remainder for biogas production. It is estimated that there is over 100 million tons of crop residues available which could be used in biogas systems.

One drawback of crop residues is that they contain lignin which is very poorly digested in biodigesters. Crop residues are typically mixed with a variety of other organic materials to generate biogas.

Composition of Biogas

The composition of biogas is dependent on the feedstock, as well as the conditions of the biodigester such as temperature, pH, organic loading rate, etc. Typical biogas composition is made up of 45-75% methane, 25-45% carbon dioxide and 5% of various other gases. It is desirable to increase the concentration of methane if it is to be used as a source of energy. Various treatments can increase the methane concentration up to 80%. But any treatment comes with an additional cost. Since produced biogas contains water vapor this must be removed prior to further application. Other gases, including carbon dioxide and hydrogen sulfide, should be removed as much as possible prior to the biogas being used as renewable natural gas.

Lignocellulosic biomass is a widely available resource which can be used in biogas production. When lignin is present in the unprocessed biomass, or in a pulp after incomplete delignification, and it is used as part of the feedstock for a biodigester, it results in a reduction of the microbial activity. This is due to lignin being highly recalcitrant to biodegradation, especially under anaerobic conditions. It has been observed that there is an inverse relationship between the amount of lignin in plant biomass and the corresponding biomethane potential, in which lignin limits the bioavailability of the more readily degradable cellulose since, as they are tightly linked together. Lignin will accumulate as the microbial community preferentially targets the more readily biodegradable compounds, which will eventually limit microbial activity. As such, it is preferable to minimize the amount of lignin remaining in the feedstock when the latter is used in anaerobic digestion for the generation of biogas in order to maximize the methane yield.

In light of the above, it is clear that biogas production needs to increase in the coming years in order to reduce countries dependence on oil and fossil fuel-based products, especially given the fact that such biogas facilities can be readily implemented. However, in order to optimize biogas production from such biogas facilities it is desirable to be able to provide a more consistent biogas output which is rich in methane. The composition of the biogas generated at such facilities may vary during the year depending on the available feedstock which is used. In many areas, farmers having a biogas facility on their farms or close by are able to provide some of the feedstock. However, some feedstock is not necessarily available year-round and thus, changing the composition of the feedstock over the year has a direct impact on the generation of biogas and the composition thereof.

Accordingly, there is a need to provide a method to generate methane-rich biogas that can account for changes in feedstock and that can employ a non-animal-based feedstock to supplement other feedstocks used in biogas production.

SUMMARY OF THE INVENTION

In accordance with the present invention, it is possible to increase the methane yield from a biodigester by carefully adjusting the biomass composition. Preferably, one adjustment which can be made is to incorporate a cellulose-rich additive which is substantially free of lignin. Preferably, a source of cellulose which is free of lignin can be generated by delignifying lignocellulosic biomass with a modified Caro's acid. Preferably, the modified Caro's acid used is as disclosed in Canadian patents 3,110,553; 3,110,555; and 3,110,558.

According to a first aspect of the present invention, there is provided a method to increase methane production from a biodigester, wherein said method comprises the addition of a biomass additive which is substantially-free of lignin.

According to a preferred embodiment of the present invention, the biomass additive is cellulose which has been processed to be substantially free of lignin.

According to another aspect of the present invention, there is provided a method to increase and stabilize the volume of methane produced from a biogas digester by using a substantially lignin-free cellulose as an additive to organic waste used for biogas production. Preferably, said substantially lignin-free cellulose is a cellulose where there remains less than 10% of the amount lignin prior to a lignocellulosic biomass being delignified. More preferably, said substantially lignin-free cellulose is a cellulose where there remains less than 5% of the amount lignin prior to a lignocellulosic biomass being delignified. Even more preferably, said substantially lignin-free cellulose is a cellulose where there remains less than 2.5% of the amount lignin prior to a lignocellulosic biomass being delignified. Yet more preferably, said substantially lignin-free cellulose is a cellulose where there remains less than 1% of the amount lignin prior to a lignocellulosic biomass being delignified.

According to a preferred embodiment of the present invention, said substantially lignin-free cellulose is present in an amount ranging up to 5 w/w of the total organic feed in the biodigester. Preferably, said substantially lignin-free cellulose is present in an amount ranging from 0.1 to 2.5 w/w of the total organic feed into the biodigester. More preferably, said substantially lignin-free cellulose and is present in an amount of ranging from 0.1 to 1 w/w of the total organic feed in the biodigester.

According to another aspect of the present invention, there is provided a process to make biogas, said process comprising the steps of:

- providing a digester adapted to receive a feed and capture a biogas composition resulting from anaerobic biodigestion;
- adding to said digester at least one organic material and at least one inoculum capable of converting a portion of said at least one organic material into methane under anaerobic conditions;
- providing a biomass which is substantially free of lignin in an amount that ranges between 0.1 to 5 w/w of the total feed;
- adding said biomass to said digester in combination with at least one other organic material;
- allowing sufficient time for the digester to degrade at least a portion of said biomass and at least a portion of said organic material to yield a biogas composition comprising methane;
- capturing said biogas composition; and
- optionally, storing said biogas.

According to another aspect of the present invention, there is provided a process to increase the amount of methane produced from a bio-digester, said method comprising the steps of:

- providing a digester adapted to receive a feed and capture a biogas composition resulting from anaerobic biodigestion;

adding to said digester at least one organic material and at least one inoculum capable of converting a portion of said at least one organic material into methane under anaerobic conditions;

providing a biomass which is substantially free of lignin in an amount that ranges between 0.1 to 5 w/w of the total feed;

adding said biomass to said digester in combination with at least one other organic material;

allowing sufficient time for the digester to degrade at least a portion of said biomass and at least a portion of said organic material to yield a biogas composition comprising methane;

capturing said biogas composition; and optionally, storing said biogas.

According to another aspect of the present invention, there is provided a use of a substantially lignin-free cellulose as additive to organic waste intended for biogas production to increase the volume of methane produced from a biogas digester, wherein said cellulose is added in an amount not exceeding 5% of the total feed in the biogas digester. Preferably, the substantially lignin-free cellulose stabilizes the volume of methane produced from a biogas digester.

According to another aspect of the present invention, there is provided a use of a substantially lignin-free cellulose as additive to organic waste intended for biogas production to decrease the volume of carbon dioxide produced from a biogas digester.

According to a preferred embodiment of the present invention, said substantially lignin-free cellulose has a particle size ranging up to 800 microns and a kappa number of less than 10. Preferably, the substantially lignin-free cellulose has a particle size ranging from 30-50 microns and a kappa number of less than 5. Preferably, substantially lignin-free cellulose has a particle size ranging from 30-50 microns and a kappa number of less than 2. According to a preferred embodiment of the present invention, said the substantially lignin-free cellulose has a particle size ranging from 30 to 50 μm in length and about 4 μm in width and a kappa number of less than 2.

According to another aspect of the present invention, there is provided a process to make biogas, said process comprising the steps of:

providing a digester adapted to receive a feed and capture a biogas composition resulting from anaerobic biodigestion;

providing a feed comprising:

at least one organic material;

at least one inoculum capable of converting a portion of said at least one organic material into methane under anaerobic conditions;

a biomass which is substantially free of lignin in an amount that ranges between 0.1 to 5 w/w of the total feed;

adding said feed to said digester;

allowing sufficient time for the feed to be degraded wherein at least a portion of said biomass and at least a portion of said organic material to yield a biogas composition comprising methane;

optionally, continuously adding said biomass which is substantially free of lignin in an amount that ranges between 0.1 to 5 w/w of the total feed comprising at least one other organic material;

capturing said biogas composition; and optionally, storing at least a portion of said biogas.

It will be understood by the person skilled in the art that biogas is generated after organic materials (plant and animal products) are broken down when exposed to microorganisms, in an anoxic environment (i.e., under anaerobic conditions). This is also referred to as anaerobic digestion. Anaerobic digestion of organic material yields biogas and residual solids and liquids which is called the digestate. The digestate is rich in nutrients that were present in the original organic material but is now more readily available for plants and soil. The composition and nutrient content of the digestate is determined by the type of feedstock used in the decomposition of the organic matter added to the digester.

According to a preferred embodiment of the present invention, there is provided a method to generate biogas which employs a substantially lignin-free cellulosic additive obtained from the exposure of a lignocellulosic feedstock to a modified Caro's acid under substantially milder conditions than other conventionally employed pulping processes (such as Kraft pulping). This approach allows for a greener process across the board as the lignocellulosic feedstock does not divert food resources away from animals or humans, as well as uses a very low energy input delignification process. According to a preferred embodiment of the present invention, the biomass additive is a cellulose wherein said cellulose has a content of hemicellulose of less than 15%, preferably less than 10% and more preferably less than 5%, and a Kappa number of less than 10, more preferably less than 5, and even more preferably, less than 2.

The biogas comprises several gases including, but not limited to, methane, carbon dioxide, hydrogen sulfide, and volatile fatty acids. In most cases, the residual solids and liquids ("digestate") can be used as fertilizer for soils.

BRIEF DESCRIPTION OF THE FIGURES

Features and advantages of embodiments of the present application will become apparent from the following detailed description and the appended figures, which.

DETAILED DESCRIPTION OF THE INVENTION

Figure 1:
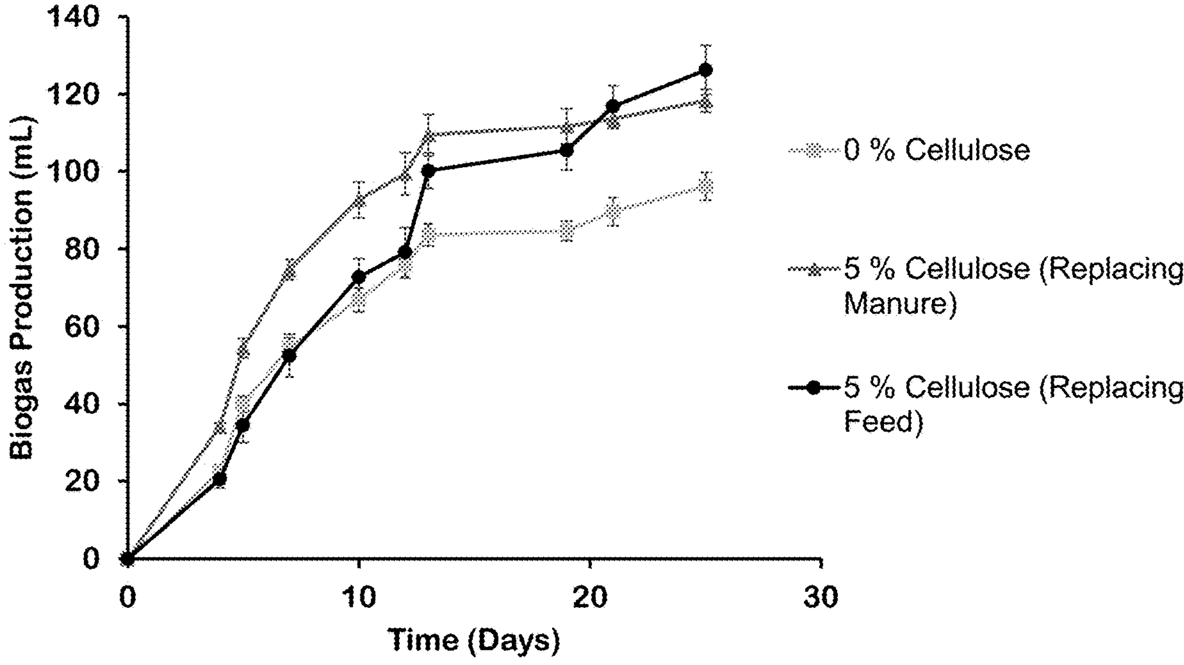
FIG. 1 is a graphical depiction of the biogas production of the samples as per experiment #1.

According to a preferred embodiment of the present invention, there is provided a method to increase the methane production from a biogas digester.

It has been surprisingly found that using a substantially lignin-free cellulose as a minor portion additive to an organic waste mass intended for biogas production when placed in a biodigester along with suitable microorganisms can increase the methane gas volume produced. It was noted that preferably, the amount of substantially lignin-free cellulose added to a biodigester yielded a disproportional amount of methane based on the mass input in the system.

According to a preferred embodiment of the present invention, there is provided a method to increase and stabilize the volume of methane produced from a biogas digester by using a substantially lignin-free cellulose as a partial additive to organic waste intended for biogas production. It has been surprisingly found that using a substantially lignin-free cellulose as a minor portion additive to an organic waste mass intended for biogas production when placed in a bio-digester along with suitable microorganisms can increase the methane gas volume produced.

According to a preferred embodiment of the present invention, the composition of gases comprises at least 60% methane to be used as an efficient source of energy.

Currently, biomass fed to anaerobic digesters is not delignified and the presence of lignin causes inhibition of the biodegradation of said biomass by microorganisms present in the biodigester and consequently hinder optimal methane production from such units. Preferably, by using cellulose obtained from a delignification of lignocellulosic biomass using a modified Caro's acid, as an additive to anaerobic digesters, the cellulose is in a more readily accessible form for the microorganisms in the biodigester.

According to a preferred embodiment of the present invention, the biomass additive is cellulose which has been processed to be substantially free of lignin.

Preferably, the addition of a substantially-free of lignin biomass additive allows for an increase in the generation of methane in a biodigester when the biomass additive is in a minor portion of the overall content of the biodigester. Preferably, the biomass additive is cellulose and is present in an amount ranging up to 5% w/w of the total organic feed in the biodigester. Preferably, the cellulose is hydrated, in some cases the water may be up to 90% of the weight of the cellulose. According to a preferred embodiment, the cellulose is present in an amount ranging from 0.1 to 5.0 w/w of the total organic feed in the biodigester. According to a preferred embodiment, said substantially lignin-free cellulose and is present in an amount ranging from 0.1 to 2.5 w/w of the total organic feed into the biodigester. According to yet another preferred embodiment, the cellulose is present in an amount of approximately 1% w/w of the total organic feed in the biodigester. Preferably, the amount of biomass additive may be adjusted based on the composition of the organic content present in the digester. It is also desirable that given the possible fluctuations between various biodigesters (due to their different organic content and microbial communities), a pre-determination be done to assess the optimal concentration of the biomass additive to be incorporated with the other organic content inside the digester so as not to incorporate an amount which is not optimal as the additive may be more costly than the other organic content inside the bio-digester.

It is generally accepted that biogas is formed mainly by the degradation of organic materials such as: carbohydrates, proteins, and lipids. The lignin fraction present in various feedstock added to digesters is known to be difficult to degrade by the microorganisms present in the digesters. While anaerobic digestion of lignin has been observed in certain environments, it requires a variety of microorganisms whose main pathway involves the enzymatic depolymerization of lignin. Even when these organisms are present, the process tends to be slow. Because of the complexity of the microbial community present in those systems, they are very difficult to reproduce on an industrial scale, making the applicability of the anaerobic digestion of lignin a complicated and difficult topic.

In Kraft pulping, about 90% of the lignin present in the processed biomass is dissolved and removed therefrom. The remaining 10% of the original lignin remains attached to the cellulose fibers and is the cause of the brown color in the unbleached pulp. If Kraft pulp was added to a biodigester, the results would not be optimal as it is known that lignin is notoriously resistant to degradation.

By adding a cellulose-rich additive which is essentially devoid of lignin, it has been made possible to increase the generation of methane in a biodigester. The delignification of biomass according to conventional approaches, such as Kraft pulping, yields a pulp which is still high in lignin. Typically, the removal of the remaining lignin is performed through a bleaching process, which involves harsh chemicals and conditions that are not energy and environmentally conscious. To employ a bleached pulp in a biodigester would simply not be commercially viable or applicable on an industrial scale as it would be cost-prohibitive.

According to a preferred embodiment of the present invention, the biomass additive is an unbleached cellulose. Preferably, the cellulose is obtained by the delignification of a biomass feedstock through the exposure of such to a modified Caro's acid as per the following processes. A preferred embodiment of the process to delignify biomass, comprises the steps of:

- providing a vessel;
- providing biomass comprising lignin, hemicellulose and cellulose fibers into said vessel;
- providing a sulfuric acid component;
- providing a peroxide component;
- exposing said biomass to said sulfuric acid and peroxide components;
- allowing said sulfuric acid and peroxide components to come into contact with said biomass for a period of time sufficient to a delignification reaction to occur and remove over 90 wt % of said lignin and hemicellulose from said biomass.

Preferably, the biomass comprising lignin, hemicellulose and cellulose fibers is exposed to a modified Caro's acid composition selected from the group consisting of: composition A; composition B and Composition C;

- wherein said composition A comprises:
  - sulfuric acid in an amount ranging from 20 to 70 wt % of the total weight of the composition;
  - a modifier compound comprising an amine moiety and a sulfonic acid moiety selected from the group consisting of: taurine; taurine derivatives; and taurine-related compounds; and
  - a peroxide;
- wherein said composition B comprises:
  - an alkylsulfonic acid; and
  - a peroxide; wherein the acid is present in an amount ranging from 40 to 80 wt % of the total weight of the composition and where the peroxide is present in an amount ranging from 10 to 40 wt % of the total weight of the composition;
- wherein said composition C comprises:
  - sulfuric acid;
  - a two-part modifier comprising:
    - a compound comprising an amine moiety; and
    - a compound comprising a sulfonic acid moiety; and
  - a peroxide.

According to a preferred embodiment of the present invention, exposing said biomass to said modified Caro's acid composition will allow the delignification reaction to occur and remove over 90 wt % of said lignin and hemicellulose from said biomass. Preferably, the substantially lignin-free cellulose was obtained from a delignification process of a lignocellulosic material in the presence of a modified Caro's acid as mentioned previously and did not undergo a drying step prior to being added to said digester. The cellulose, once obtained, is not dried and so is more bioavailable than a dried cellulose. This may be attributed to the absence, or at least reduction, of hornification within the cellulose obtained after the delignification process. Cellulose hornification is the resulting loss of swelling of the cellulose fibre wall due to a drying of the cellulose. The result of drying cellulose includes the stiffening of cellulosic fibres which, in turn, reduces their ability to form inter-fibre bonds.

Preferably, the delignification reaction is carried out at a temperature below 55° C. by a method selected from the group consisting of:

adding water into said vessel;

adding biomass into said vessel; and using a heat exchanger.

Preferably, said sulfuric acid, said compound comprising an amine moiety and a sulfonic acid moiety and said peroxide are present in a molar ratio of no less than 1:1:1. Also preferably, said sulfuric acid, said compound comprising an amine moiety and a sulfonic acid moiety and said peroxide are present in a molar ratio of no more than 15:1:1.

According to a preferred embodiment of the present invention, said sulfuric acid and said compound comprising an amine moiety and a sulfonic acid moiety are present in a molar ratio of no less than 3:1.

According to a preferred embodiment of the present invention, said compound comprising an amine moiety and a sulfonic acid moiety is selected from the group consisting of: taurine; taurine derivatives; and taurine-related compounds.

According to a preferred embodiment of the present invention, said taurine derivative or taurine-related compound is selected from the group consisting of: taurolidine; taurocholic acid; tauroselcholic acid; tauromustine; 5-taurinomethyluridine and 5-taurinomethyl-2-thiouridine; homotaurine (tramiprosate); acamprosate; and taurates; as well as aminoalkylsulfonic acids where the alkyl is selected from the group consisting of $C_1$-$C_5$ linear alkyl and $C_1$-$C_5$ branched alkyl. Preferably, said linear alkylaminosulfonic acid is selected form the group consisting of: methyl; ethyl (taurine); propyl; and butyl. Preferably, said branched aminoalkylsulfonic acid is selected from the group consisting of: isopropyl; isobutyl; and isopentyl.

According to a preferred embodiment of the present invention, said compound comprising an amine moiety and a sulfonic acid moiety is taurine.

According to a preferred embodiment of the present invention, said sulfuric acid and compound comprising an amine moiety and a sulfonic acid moiety are present in a molar ratio of no less than 3:1.

According to a preferred embodiment of the present invention, said compound comprising an amine moiety is an alkanolamine is selected from the group consisting of: monoethanolamine; diethanolamine; triethanolamine; and combinations thereof.

According to a preferred embodiment of the present invention, said compound comprising a sulfonic acid moiety is selected from the group consisting of: alkylsulfonic acids and combinations thereof.

According to a preferred embodiment of the present invention, said alkylsulfonic acid is selected from the group consisting of: alkylsulfonic acids where the alkyl groups range from $C_1$-$C_6$ and are linear or branched; and combinations thereof.

According to a preferred embodiment of the present invention, said alkylsulfonic acid is selected from the group consisting of: methanesulfonic acid; ethanesulfonic acid; propanesulfonic acid; 2-propanesulfonic acid; isobutylsulfonic acid; t-butylsulfonic acid; butanesulfonic acid; iso-pentylsulfonic acid; t-pentylsulfonic acid; pentanesulfonic acid; t-butylhexanesulfonic acid; and combinations thereof.

According to a preferred embodiment of the present invention, said alkylsulfonic acid; and said peroxide are present in a molar ratio of no less than 1:1.

According to a preferred embodiment of the present invention, said compound comprising a sulfonic acid moiety is methanesulfonic acid.

According to a preferred embodiment of the present invention, in Composition C, said sulfuric acid and said a compound comprising an amine moiety and said compound comprising a sulfonic acid moiety are present in a molar ratio of no less than 1:1:1.

According to a preferred embodiment of the present invention, in Composition C, said sulfuric acid, said compound comprising an amine moiety and said compound comprising a sulfonic acid moiety are present in a molar ratio ranging from 28:1:1 to 2:1:1.

According to a preferred embodiment of the present invention, the biomass additive is a cellulose wherein said cellulose has a content of hemicellulose of less than 15%, preferably less than 10% and more preferably less than 5%, and a Kappa number of less than 10, more preferably less than 5, and even more preferably, less than 2.

Lab Scale Testing

Serum bottles were used to conduct anaerobic digestion experiments. The serum bottles were set up by adding manure, inoculum (digestate from a commercial scale digester) and feedstock comprised of agricultural waste and/or cellulose obtained via a delignification process involving the use of a modified Caro's acid as described earlier. Each serum bottle batch was set to run under mesophilic conditions. Biogas production and methane concentrations were regularly measured throughout the experiment. FOS/TAC measurements (measure of volatile fatty acids and total organic carbon; a standard in the industry for evaluating the balance of the digester) were taken throughout the experiments.

According to a preferred embodiment of the present invention, the cellulose is a low kappa number cellulose, wherein said a low kappa number cellulose has the following characteristics: particle size ranging up to 800 microns and a kappa number of less than 10, more preferably less than 5 and even more preferably, less than 2.

Experiment #1—Determination of the Effect of a Substantially Lignin-Free Cellulose Additive For the first batch, the basic proof-of-concept was tested to confirm if the presence of low-lignin content cellulose increases methane production in the system. Also, one could evaluate the performance of replacing a portion of the manure with cellulose (45% manure instead of 50% manure) or replacing a portion of the agricultural waste feedstock (15% feedstock instead of 20%) with cellulose would be more efficient.

The cellulose used in the experiments has an aspect ratio of about 7.5. The aspect ratio of a particle, in this case, cellulose fibers, is determined by the ratio of its length over its width. In the above case, the particles are about 30 to 50 μm in length and about 4 μm in width.

This was tested by preparing the following samples (n=4):

1. Inoculum only (n=1)
2. 0% Cellulose, cow manure
3. 5% Cellulose, replacing manure
4. 5% Cellulose, replacing feedstock Each sample contained 50% manure, aside from sample 4, (45% manure) and all samples contained 20% inoculant. The feedstock used was a combination of potatoes, floatation screenings, and other various agricultural wastes. Samples were incubated at 40° C.

Figure 2:
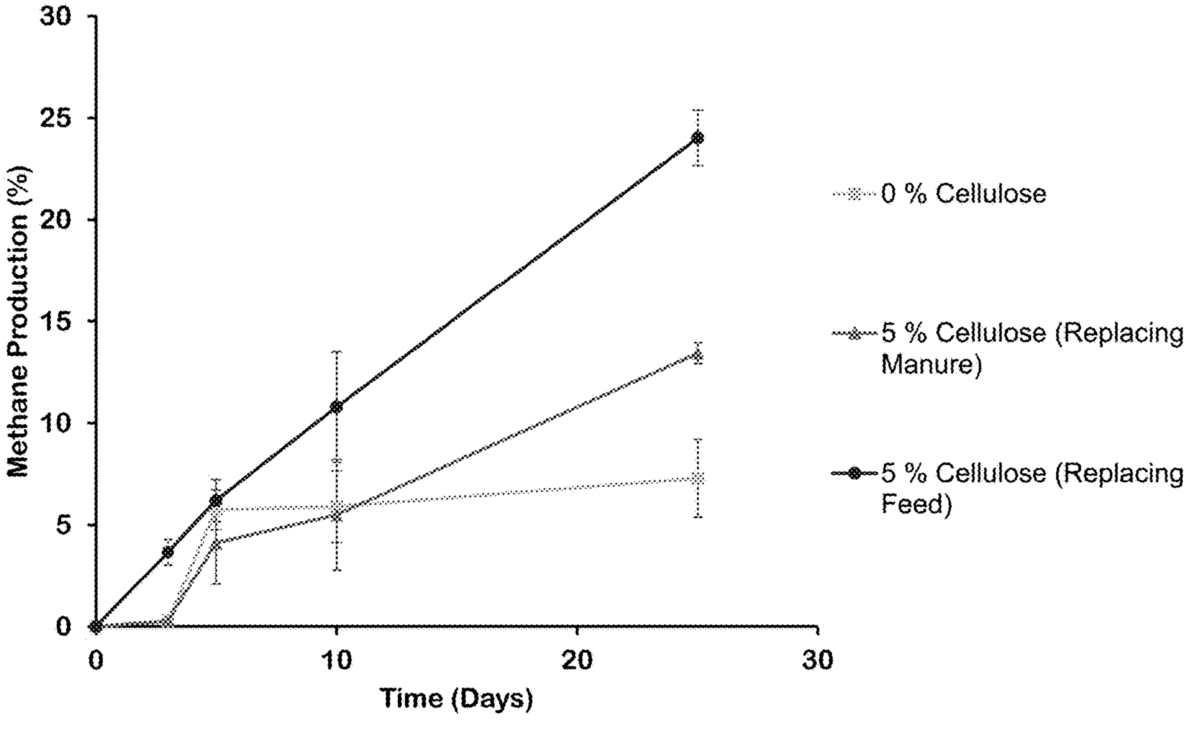
FIG. 2 is a graphical depiction of the methane percentage of the samples as per experiment #1.

It was observed throughout the experiment that the cellulose-containing samples produced more biogas than the non-cellulose containing samples (FIG. 1). Methane concentrations were immediately highest in the cellulose replacing a portion of feed samples and this trend continued throughout the month. Methane concentrations in the samples with cellulose replacing a portion of feed were consistently higher than all other samples. By day 10, the methane concentration spiked in the cellulose replacing a portion of manure samples as well but did not continue to increase nearly as much as the cellulose replacing feed samples did (FIG. 2).

Experiment #2—Determination of Chemical Oxygen Demand (COD) and Biomethane Potential (BMP)

COD is a measure of the amount of oxygen that can be consumed by reactions in the digester. It is used to calculate BMP. BMP is a characteristic of a substrate that defines the maximum amount of methane that can be produced by anaerobic digestion. It is typically measured in mL of methane per gram of volatile solids of the substrate. This value is commonly discussed in the biogas community when talking about the value of potential feeds. BMP is usually tested in a laboratory in serum bottles or through automated BMP test equipment.

An experiment was carried out to obtain biomethane potential (BMP) of the substantially lignin-free cellulose and compare it to the BMP of a common lignocellulosic digester feed (straw).

The substrate (cellulose or straw) is digested in a bottle containing digestate (inoculum) alongside blank bottles containing only digestate. The resulting methane value obtained from the blank is subtracted from the methane value obtained from the substrate-containing bottles to get the final cumulative methane production from the substrate alone.

Substrates were tested at a 0.1:1 substrate to digestate ratio. The chemical oxygen demand (COD), theoretical BMP, and volatile solids (VS) of each substrate were measured. Biogas production in the bottles wase measured over 78 days. Results are shown in Table 1.

TABLE 1

Chemical oxygen demand (COD), theoretical BMP, and volatile solids (VS) of each substrate

| Substrate | Chemical Oxygen Demand (mg/L) | Volatile Solids (%) | Theoretical Methane Potential (mL/g VS) |
|---|---|---|---|
| Straw | 21500 | 94 | 152 |
| Cellulose | 18800 | 99 | 518 |
| Digestate | 50500 | 74 | 24 |

Figure 3:
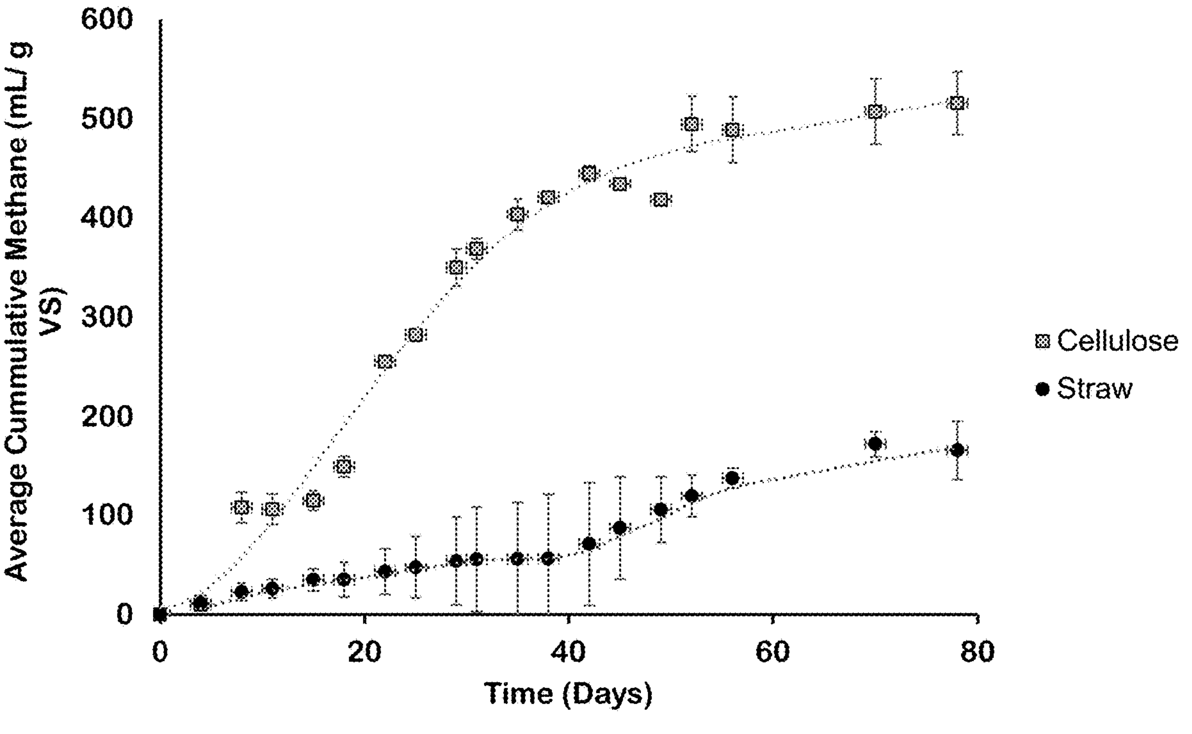
FIG. 3 is a graphical depiction of the cumulative methane in mL/g VS of the substantially lignin-free cellulose compared it to a common lignocellulosic digester feed (straw), as per experiment #2.

Table 1 shows that the cellulose has a significantly higher theoretical biomethane potential (BMP) than straw, a common agricultural waste material used in farm anaerobic digesters. In experimental BMP tests, these results were confirmed, where the average cumulative millilitres of methane produced per gram of volatile solids is significantly higher in substantially lignin-free cellulose than in straw (FIG. 3). This suggests that the potential for methane production per gram of substantially lignin-free cellulose is significantly higher than that of the potential for methane production per gram of straw. To get the same methane production, a much higher volume of straw would be required to feed into the digester than the cellulose. This suggests that small amounts of substantially lignin-free cellulose could be fed into an anerobic digestive system to result in significant increases in methane production.

Experiment #3—Determination of Methane Production on Lab Scale

Figure 4:
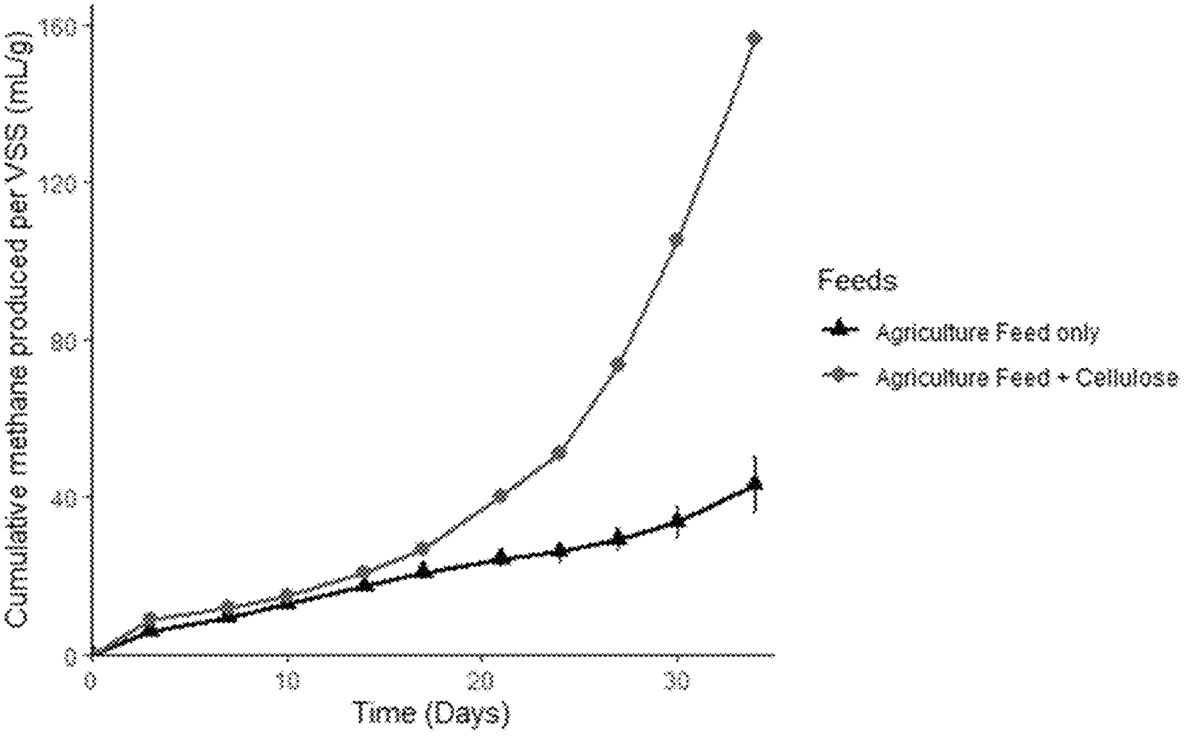
FIG. 4 is a graphical depiction of the methane production of the samples as per experiment #3.

Serum bottles were filled with digestate, manure and agricultural feeds. A substantially lignin-free cellulose additive was added to some of the bottles, substituting part of the agricultural feedstock. Methane concentration was measured over time using a GC-FID. Biogas generation was monitored throughout the experiment. The results of the test are found in FIG. 4.

The bottles contained roughly 7 g of manure and agricultural feed combined, in the case of the cellulose the agricultural feed was partially replaced by the cellulose to achieve the same mass. The cellulose was present in an amount of approximately 3.5% of the total combined feed. The bottles that contained the substantially 0.5% of the whole system lignin-free cellulose supplement produced nearly 4 times more methane per gram of volatile solids, as compared with no supplementation.

Field Trial

A field trial was conducted in two 2,112 $m^3$ anaerobic digesters, which are connected. The digesters can process over 17,000 tonnes of organic waste per year, which includes manure, crop silage, as well as organic cull and waste. The trial lasted 3 weeks (with no changes in the feed) and the biodigesters were monitored for a period of 7 weeks.

Observation on the Biogas Composition During Trial

Figure 5:
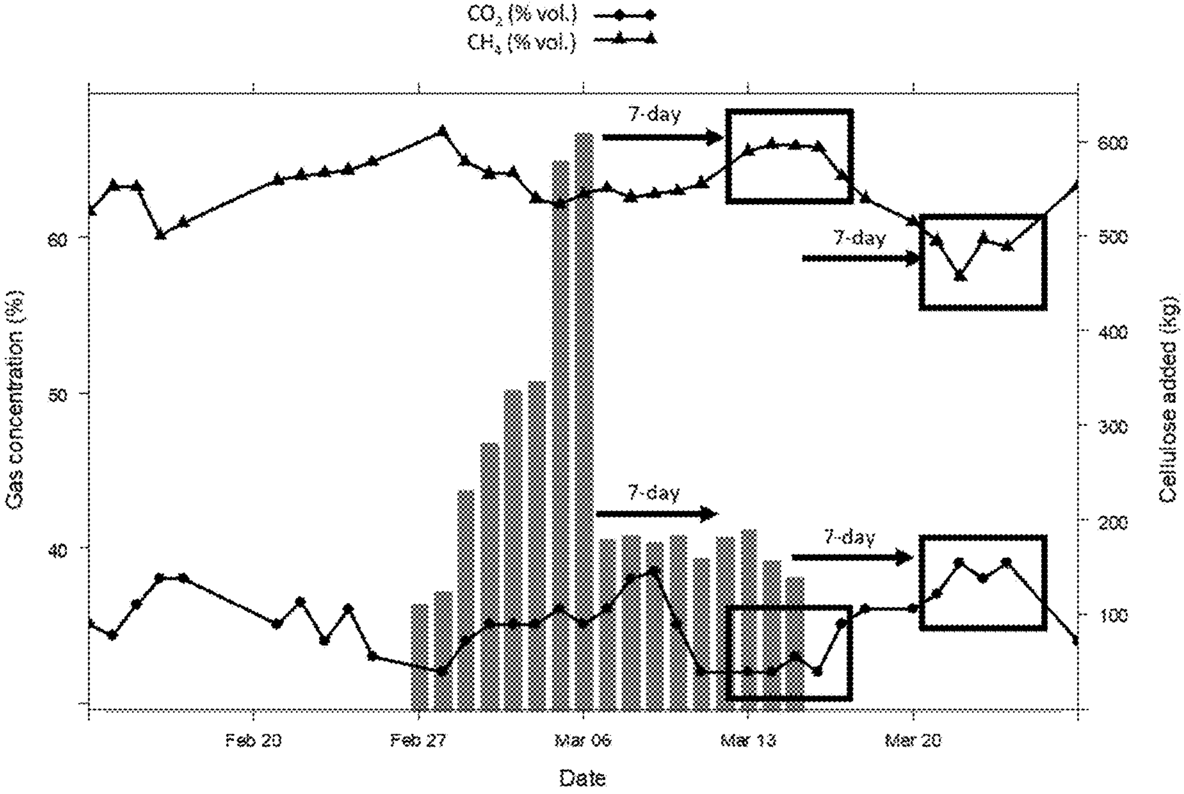
FIG. 5 is a graphical depiction of the biogas production and substantially lignin-free cellulose addition over time in the field trial.

It was observed that there was a short 7-day delay between cellulose peak addition and changes in biogas composition (FIG. 5). As the cellulose is metabolized by the microorganisms in the digester, several members of the microbial community will be syntrophic. A syntrophic microbial community is one that contains many different types of microorganisms that have different metabolic pathways, and the products of these different metabolic pathways benefit other microbes in the community. In this type of interaction, metabolites of the cellulose will be transferred between two or more metabolically diverse microorganisms. The growth of one microbe depends on the nutrients, growth factors, or substrates provided by the other microbe. Cellulose will be biodegraded into smaller saccharides (such as cellobiose or glucose). These saccharides will then be fermented by acetogenic microorganisms into acids and carbon dioxide, and these products can then be converted to methane by methanogenic archaea. The delay initially observed is likely due to the time it takes for all these processes to occur. It was noted that there was a sustained methane concentration increase and carbon dioxide decrease (approx. 5-10% with respect to baseline) after addition of cellulose. Also observed was a sharp decrease in methane (>10%) and corresponding increase in carbon dioxide (>20%) after cellulose feeding was halted with the same 7-day delay. During the trial, biogas production was constant with no significant changes, indicating that the increase in methane % corresponds to an increase in volume of methane generated. From the data collected during this trial, it becomes clear that the use of cellulose as an additive lead to a sustained increase in methane production, as well as a decrease in the carbon dioxide portion of the biogas produced.

The above results substantiate the use of a substantially lignin-free cellulose as additive to organic waste intended for biogas production to increase the volume of methane produced from a biogas digester, wherein said cellulose is added in an amount not exceeding 5% of the total feed in the biogas digester. The above results also substantiate the use of a substantially lignin-free cellulose as an additive to stabilize the volume of methane produced from a biogas digester. Further, the above results also support the use of a substantially lignin-free cellulose as additive to organic waste intended for biogas production to decrease the volume of carbon dioxide produced from a biogas digester.

Figure 6:
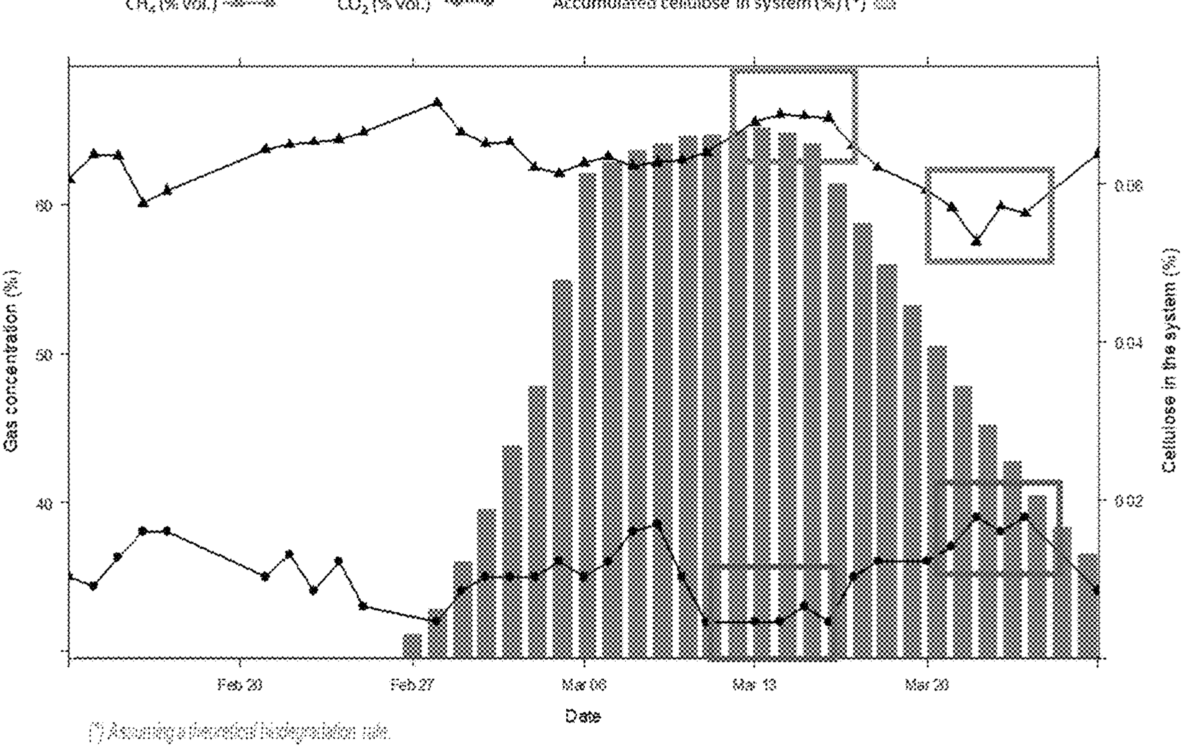
FIG. 6 is a graphical depiction of the biogas production and substantially lignin-free cellulose accumulation and theoretical biodegradation over time in the field trial.

The changes in biogas observed in FIG. 6 align with the use of cellulose as an additive and the theoretical cellulose biodegradation calculated from the experimental BMP tests mentioned above (FIG. 3).

FOS/TAC Ratio Observed During Trial

The FOS/TAC ratio is an indicator for assessing fermentation processes. The FOS/TAC value is the ratio of volatile organic acids (or "Flüchtige Organische Säuren", FOS, in German) to the total alkalinity or buffering ability of the anaerobic digestion system (or "Total Anorganic Carbon", TAC, in German). Anaerobic digestion has four typical microbial transformations: hydrolysis, acidogenesis, acetogenesis, and methanogenesis. During the acidogenesis, the compounds obtained from the hydrolysis stage (i.e., sugars, amino acids, etc.) are degraded by acidogenic microorganisms to produce volatile fatty acids (VFAs) such as acetic, propionic, and butyric acids. These VFAs are then consumed by acetogenic and methanogenic microorganisms for the production of biogas and, thus, methane. When VFAs start to accumulate, the buffering ability of the digester (the TAC portion of the ratio) becomes a crucial parameter to counter the low pH of VFAs and maintain an optimal pH, which is critical for the success of a correct functioning of the anaerobic digesters.

A FOS/TAC ratio of 0.3-0.4 is optimal for peak biogas production in anaerobic digesters. This ratio is an excellent indicator of digester health, as it provides a guideline for the volume of feed the digester needs, the stability of the microbial community, and the potential accumulation of volatile organic acids. The FOS/TAC ratio will be affected by changes in feeding rate, feeding composition, mixing, temperature, pH, and microbial community shift.

By supplying a consistent carbon source, even at low supplementary amounts, the addition of a cellulose-rich additive which is essentially devoid of lignin, allowed an optimal FOS/TAC ratio to be achieved. When the supplementation was decreased, the FOS/TAC ratio subsequently fell outside of the optimal range. A consistent supplementation using cellulose additive which is essentially devoid of lignin will allow for a potentially more stable syntrophic microbial community. The numerous microorganisms working simultaneously to convert the biological waste to biogas can be maintained more steadily when supplied with this readily accessible carbon source. Table 2 highlights the various ranges of ratios and the signs of biodigester health.

TABLE 2

FOS/TAC ratios and their indication of biodigester health

| FOS/TAC Ratio | Biodigester Indication |
|---|---|
| >0.6 | Highly excessive biomass input |
| 0.5-0.6 | Excessive biomass input |
| 0.4-0.5 | Slightly too much biomass input |
| 0.3-0.4 | Optimal biogas production |
| 0.2-0.3 | Insufficient biomass input |
| <0.2 | Insufficient biomass input |

Figure 7:
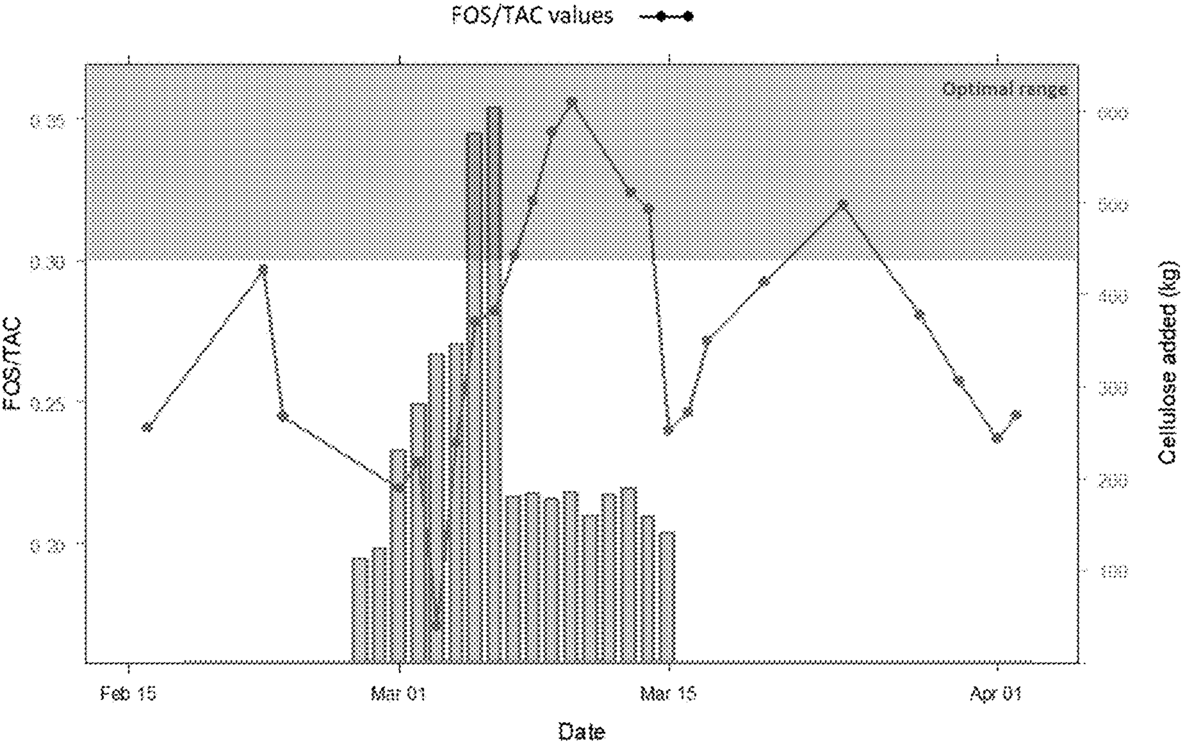
FIG. 7 is a is a graphical depiction of the FOS/TAC ratio and substantially lignin-free cellulose addition over time in the field trial.

In referring to FIG. 7, it can be observed that the FOS/TAC value of the biogas produced is consistently lower than the optimal range prior to the beginning of the trial. It is observed that the FOS/TAC ratio increases steadily to a achieve the optimal level (i.e., healthy level) with the addition of the cellulose.

Addition of the cellulose-rich additive which is essentially devoid of lignin as a supplement leads to a FOS/TAC ratio within the optimal range. It is important to be able to maintain the FOS/TAC, ratio in the optimal range, which is not easy to do when the feedstock which is added to the bioreactor varies depending on the availability thereof. It is established on referring to FIG. 7 that the addition of the cellulose supplement for anaerobic digestion increased the health of the anaerobic digestion, leading to better FOS/TAC ratios and an increase in methane content in the resulting produced biogas stream.

According to a preferred embodiment of the present invention, the cellulose additive for anaerobic digestion is only needed at a minimal loading of the total daily feed (comprising the organic material+ cellulose) (<0.3%) of the anaerobic digester for significant sustained benefits.

While the foregoing invention has been described in some detail for purposes of clarity and understanding, it will be appreciated by those skilled in the relevant arts, once they have been made familiar with this disclosure that various changes in form and detail can be made without departing from the true scope of the invention in the appended claims.

The invention claimed is:

1. A method to increase and stabilize the volume of methane produced from a biogas digester by using a substantially lignin-free and unbleached cellulose as an additive to organic waste used for biogas production wherein the substantially lignin-free and unbleached cellulose is obtained by a delignification process comprising the steps of:

providing a vessel;

providing a biomass comprising lignin, hemicellulose and cellulose fibers into said vessel;

providing a sulfuric acid component;

providing a peroxide component;

exposing said biomass to said sulfuric acid and peroxide components;

allowing said sulfuric acid and peroxide components to come into contact with said biomass for a period of time sufficient to a delignification reaction to occur and remove over 90 wt % of said lignin; and hemicellulose from said biomass.

2. The method according claim 1 wherein said substantially lignin-free cellulose is a cellulose comprising less than 5% of lignin.

3. The method according claim 1 wherein said substantially lignin-free cellulose is a cellulose comprising less than 2.5% of lignin.

4. The method according to claim 1 wherein said substantially lignin-free cellulose is a cellulose comprising less than 1% of lignin.

5. The method according to claim 1 wherein said lignin-free cellulose is present in an amount ranging up to 5% w/w of the total organic feed in the biodigester.

6. The method according to claim 1 wherein said lignin-free cellulose and is present in an amount ranging from 0.1 to 2.5% w/w of the total organic feed into the biodigester.

7. The method according to claim 1 wherein said lignin-free cellulose and is present in an amount of ranging from 0.1 to 1% w/w of the total organic feed in the biodigester.

8. A process to make biogas, said process comprising the steps of:

providing a digester adapted to receive a feed and capture a biogas composition resulting from biodigestion;

adding to said digester at least one organic material and at least one inoculum capable of converting a portion of said at least one organic material into methane under anaerobic conditions;

providing a biomass which is substantially free of lignin in an amount that ranges between 0.1 to 5% w/w of the total feed, comprising at least one other organic material;

adding said biomass to said digester;

allowing sufficient time for the digester to degrade at least a portion of said biomass and at least a portion of said organic material to yield a biogas composition comprising methane;

optionally, continuously adding said biomass which is substantially free of lignin in an amount that ranges between 0.1 to 5% w/w of the total feed comprising at least one other organic material;

capturing said biogas composition;

optionally, storing said biogas; and wherein the biogas is methane that is produced by using a substantially lignin-free and unbleached cellulose as an additive and further wherein the substantially lignin-free and unbleached cellulose is obtained by a delignification process.

9. A process to increase the amount of methane produced from a bio-digester, said method comprising the steps of:

providing a digester adapted to receive a feed and capture a biogas composition resulting from biodigestion;

adding to said digester at least one organic material and at least one inoculum capable of converting a portion of said at least one organic material into methane under anaerobic conditions;

providing a biomass which is substantially free of lignin in an amount that ranges between 0.1 to 5% w/w of the total feed, comprising at least one other organic material;

adding said biomass to said digester;

allowing sufficient time for the digester to degrade at least a portion of said biomass and at least a portion of said organic material to yield a biogas composition comprising methane;

continuously adding said biomass which is substantially free of lignin in an amount that ranges between 0.1 to 5% w/w of the total feed comprising at least one other organic material wherein the biomass includes unbleached cellulose as an additive and further wherein the substantially lignin-free and unbleached cellulose is obtained by a delignification process;

capturing said biogas composition; and optionally, storing said biogas.

10. The method according claim 1 wherein the biomass comprising lignin, hemicellulose and cellulose fibers is exposed to said sulfuric acid and peroxide components, said sulfuric acid and peroxide components selected from the group consisting of at least one of: composition A; composition B and composition C;

wherein said composition A comprises:

sulfuric acid in an amount ranging from 20 to 70 wt % of the total weight of the composition;

a modifier compound comprising an amine moiety and a sulfonic acid moiety selected from the group consisting of: taurine; taurine derivatives;

and taurine-related compounds; and a peroxide;

wherein said composition B comprises:

an alkylsulfonic acid; and a peroxide; wherein the acid is present in an amount ranging from 40 to 80 wt % of the total weight of the composition and where the peroxide is present in an amount ranging from 10 to 40 wt % of the total weight of the composition;

wherein said composition C comprises:

sulfuric acid;

a two-part modifier comprising:

a compound comprising an amine moiety; and a compound comprising a sulfonic acid moiety; and a peroxide.

* * * * *